(12) United States Patent
Matter et al.

(10) Patent No.: US 6,614,242 B2
(45) Date of Patent: Sep. 2, 2003

(54) METHOD AND DEVICE FOR OIL-IN-WATER MEASUREMENT

(75) Inventors: Daniel Matter, Brugg (CH); Walter Rüegg, Endingen (CH); Thomas Kleiner, Fislisbach (CH); John Anthony Byatt, Klingnau (CH)

(73) Assignee: ABB Research Ltd, Zurich (CH)

( * ) Notice: Subject to any disclaimer, the term of this patent is extended or adjusted under 35 U.S.C. 154(b) by 0 days.

(21) Appl. No.: 09/732,009

(22) Filed: Dec. 8, 2000

(65) Prior Publication Data

US 2001/0003426 A1 Jun. 14, 2001

(30) Foreign Application Priority Data

Dec. 8, 1999 (DE) .......................... 199 59 005

(51) Int. Cl.[7] .................. G01R 27/08; G01R 27/26; G01R 35/00; G01N 27/02; G01N 27/26
(52) U.S. Cl. .................. 324/698; 324/686; 324/448; 324/601; 204/400; 204/406
(58) Field of Search ................. 324/698, 694, 324/686, 691, 71.1, 439, 601, 448; 204/406, 193, 400; 73/61.44, 1.02, 53.05

(56) References Cited

U.S. PATENT DOCUMENTS

| 4,034,219 A | 7/1977 | Louden et al. | |
|---|---|---|---|
| 4,057,721 A | 11/1977 | deVial et al. | |
| 4,137,494 A | * 1/1979 | Malley et al. | 204/406 |
| 4,598,280 A | * 7/1986 | Bradford | 324/698 |
| 4,686,857 A | * 8/1987 | Kato | 324/698 |
| 4,907,442 A | * 3/1990 | Jones et al. | 324/376 |
| 5,523,692 A | * 6/1996 | Kuroyanagi et al. | 324/438 |
| 5,907,278 A | * 5/1999 | Park et al. | 123/196 M |
| 5,973,503 A | * 10/1999 | Kuipers et al. | 324/439 |

FOREIGN PATENT DOCUMENTS

GB  2 322 937  3/1977

* cited by examiner

*Primary Examiner*—Anjan K. Deb
(74) *Attorney, Agent, or Firm*—Burns, Doane, Swecker & Mathis, L.L.P.

(57) ABSTRACT

A method and a sensor (1) for oil-in-water measurement, in particular for the oil industry. In an electric measuring cell (7, 12) a capacitance is measured as a measure of an oil concentration in the water flowing through or in the accumulation filter (16, 16a, 16b). In order to reduce the maintenance requirement, the measuring cell (7, 12) is automatically calibrated at recurring time intervals with clean water (FIG. 1) and/or flushed with water, possibly oil-contaminated, in the back-flushing direction (FIG. 2). Advantages of the invention are reduced signal drift, improved long-term reliability and a long service life without monitoring or filter exchange. Important exemplary embodiments relate to: a measuring cell (7, 12) with a long measuring and short flushing/calibration cycle, a measuring cell (7, 12) with a plurality of accumulation filters (16a, 16b) whose measuring cycles supplement one another in time, a cross-flow filter (2) for oil enrichment upstream of the measuring cell (7, 12) and a compact, pressure-resistant cylindrical ring-type filter (13) made from porous ceramic (16, 16a, 16b) with measuring and flushing connections radially (17a, 17b, 18a, 18b) and axially (17c, 18c).

26 Claims, 5 Drawing Sheets

METHOD AND DEVICE FOR OIL-IN-WATER MEASUREMENT

This application claims priority under 35 U.S.C. §§119 and/or 365 to Appln. No. 199 59 005.2 filed in Germany on Dec. 8, 1999; the entire content of which is hereby incorporated by reference.

TECHNICAL FIELD

The present invention relates to the field of measurement of small oil concentrations in water. It proceeds from a method and a device for oil-in-water measurement according to the preamble of claims 1 and 6.

PRIOR ART

High-pressure separator tanks have recently been developed for offshore oil production which are suitable for separating the phases of sand, water, oil and gas directly at the seabed. According to statutory provisions, the water pumped back into the sea may have an oil concentration of at most a few 10 ppm. Although conventional capacitive or optical oil-in-water sensors can achieve such high measuring sensitivity in principle, it is not possible to achieve the required freedom from maintenance, long service life and pressure and temperature resistance.

Such a device for determining a low oil concentration in water is disclosed in U.S. Pat. No. 4,137,494. The measuring cell consists of an oil-absorbing diaphragm with electrodes mounted on both sides. Oil molecules contained in the water penetrate into the diaphragm, displace ions embedded there and increase the electric resistance of the diaphragm. The change in resistance is then a measure of the oil concentration in the water flowing through. In order to raise the measuring sensitivity, a water sample has to be pumped into a closed circuit repeatedly through the diaphragm in order to absorb all the oil there. The method has substantial disadvantages. As soon as the total amount of oil accumulated reaches a saturation value, the diaphragm must be disposed of or flushed with a solvent for the purpose of regeneration. Consequently, periodic maintenance intervals are stringently required, and this renders difficult or impossible installation at inaccessible sites, for example on the seabed. The measurement can also be falsified by a variable ion concentration in the water.

SUMMARY OF THE INVENTION

It is the object of the present invention to specify a method and a sensor for oil-in-water measurement in the case of which it is possible to implement a high measuring accuracy in conjunction with a greatly reduced maintenance requirement. This object is achieved according to the invention by means of the features of claims 1 and 6.

The solution according to the invention consists in a method and a device for oil-in-water measurement having a measuring cell whose impedance is a measure of an oil concentration in the water flowing through or in an accumulation filter, the measuring cell being automatically calibrated and/or flushed at recurring time intervals. During calibration, a current reference impedance value of the measuring cell is measured with the aid of a known reference liquid. The measuring cell is automatically cleaned of oil residues during flushing. Both self-calibration and self-flushing are carried out by a suitably designed or programmed electronic control system. Advantages are, inter alia, a reduction in signal drift, an improved long-term reliability and a long service life without monitoring or filter exchange. Overall, for the first time, an oil-in-water sensor is specified which is suitable for use at poorly accessible locations in oil production or the like.

In accordance with an exemplary embodiment, the measuring cell is operated in an alternating fashion in a long measuring cycle (for example 10 minutes) and a short flushing cycle (for example 1 minute) and/or an even shorter calibration cycle. The measuring cell preferably has two or more accumulation filters whose measuring cycles supplement one another such that a measuring signal can be determined in the measuring cell largely at any instant. This delivers a high degree of availability of the measuring cell for online measurements.

One exemplary embodiment relates to an oil-in-water sensor having a cross-flow filter whose output for oil-enriched water is connected to a capacitive measuring cell during the measuring cycle and whose output for cleaned water is connected to a capacitive measuring cell during the calibration cycle. The measuring sensitivity can be raised and the calibration liquid can be provided in the simplest way by the separating filter.

In another exemplary embodiment, there is arranged in a capacitive measuring cell an oil accumulation filter which can be flowed through in the reverse direction for flushing purposes by a valve-controlled line system. Owing to the reversal of direction during the flushing operation, oil residues or a filter cake on the filter outer surface, that is to say on the inlet side during the measuring cycle, can also be flushed out very efficiently with oil-contaminated water.

In an important exemplary embodiment, the oil accumulation filter is a cylindrical ring-type filter made from porous ceramic or polyethylene fibrid which has at least one radial and one axial connection. The cylindrical form creates a mechanically robust, compact and simultaneously large-area accumulation filter. In addition, it is possible by segmenting the electrodes on the outer and inner cylinder outer surface to implement a plurality of filters on a common ceramic body which run through measuring cycles which supplement one another in time, intermittent flushing cycles and/or cycles for determining offset. The self-flushing and self-calibration can thereby be implemented in a single component.

Further designs, advantages and applications of the invention follow from the dependant claims and from the description now following, in conjunction with the figures.

BRIEF DESCRIPTION OF THE DRAWINGS

In the drawings.

Identical parts are provided in the figures with identical reference numerals.

WAYS OF IMPLEMENTING THE INVENTION

The subject matter of the invention is a method for oil-in-water measurement which is suitable, in particular, for measuring an oil concentration in water in a high-pressure separator tank. A measuring cell 7, 12 is fed oil-contaminated water, and an electric impedance signal of the measuring cell 7, 12 is measured. According to the invention, the measuring cell 7, 12 is calibrated and/or flushed automatically at periodic intervals. Exemplary embodiments relating to the method are specified below with general reference to FIGS. 1–3.

Figure 1:
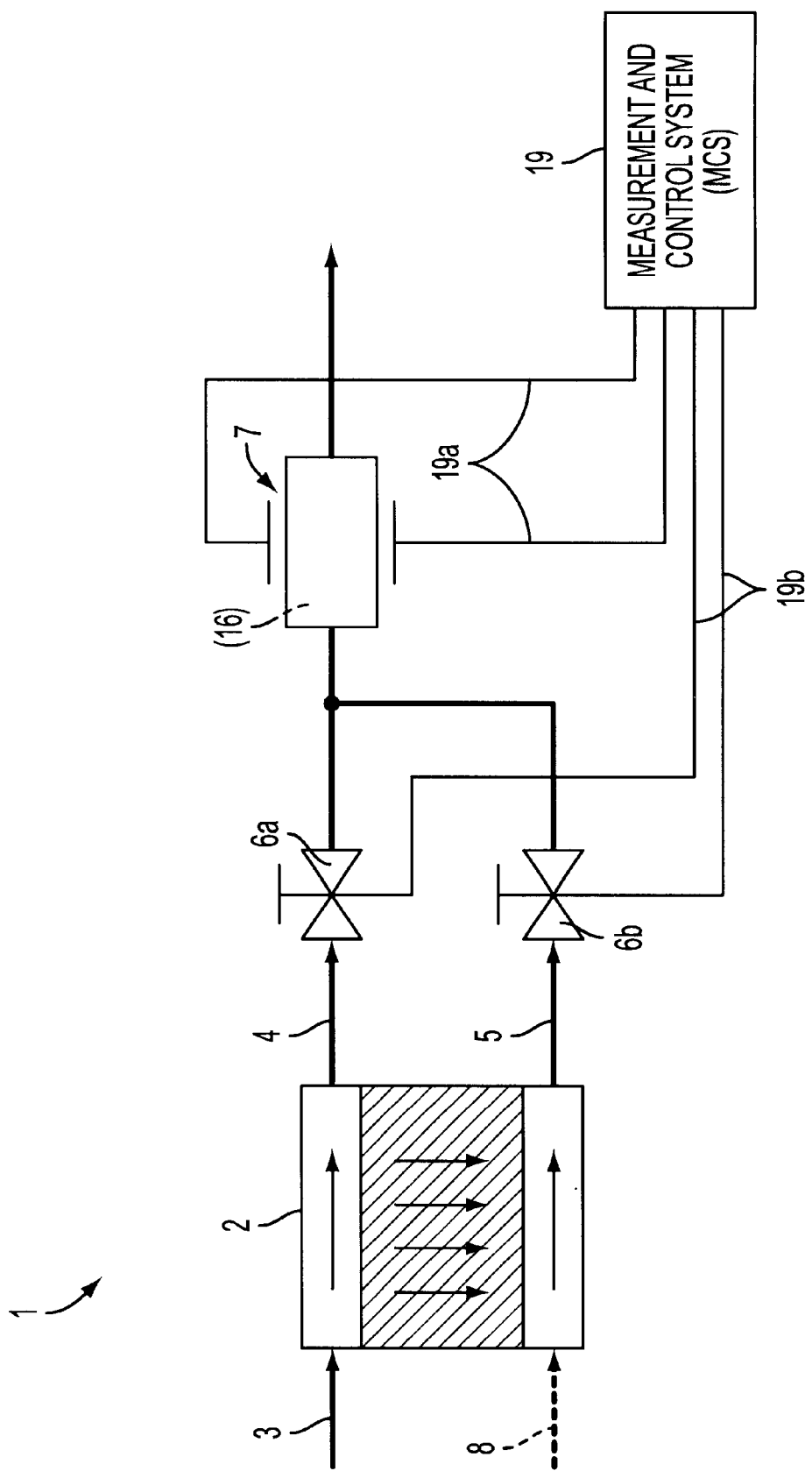
FIG. 1 shows an oil-in-water sensor according to the invention with a cross-flow filter for oil enrichment for a capacitive throughflow measuring cell.
Figure 2:
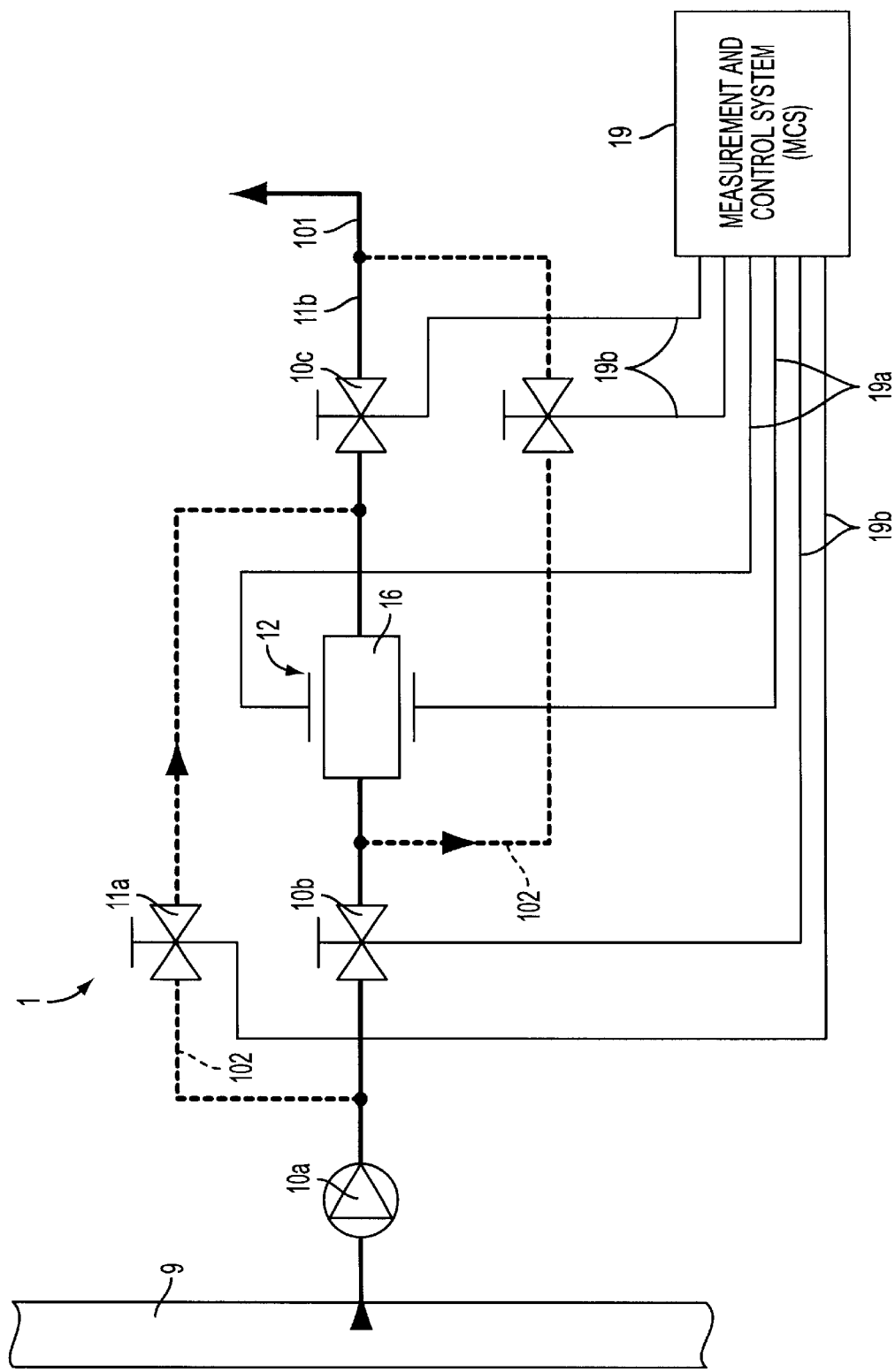
FIG. 2 shows an oil-in-water sensor according to the invention which has a capacitive measuring cell with an oil-accumulating ceramic filter.
Figure 3A:
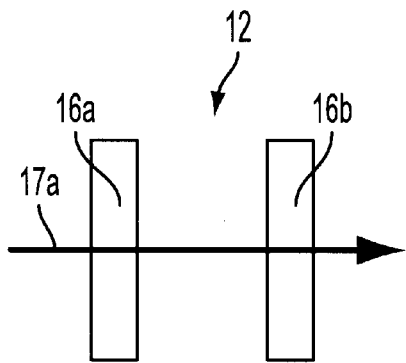
FIG. 3 shows a serial arrangement according to the invention of two oil accumulation filters for simultaneous measurement and flushing and for independent offset measurement and FIG. 4 shows a capacitive measuring cell according to the invention with a ring-type filter.
Figure 3B:
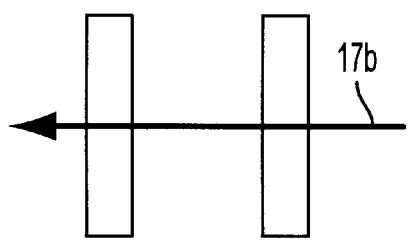
Figure 3C:
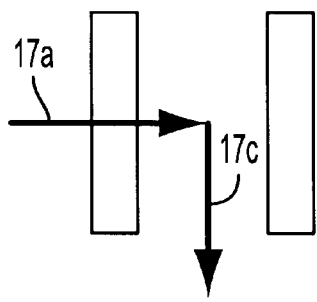
Figure 3D:
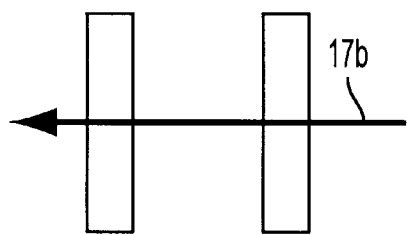

During calibration, the measuring cell 7, 12 is flowed through by clean water and a calibration signal is formed (FIG. 1). During flushing, the measuring cell 12 is flowed through backward by water (FIG. 2). According to the invention, the reverse flushing can be carried out even with oil-contaminated water. The oil-in-water sensor, for example for applications in the oil industry, is thereby significantly simplified and the everyday usefulness is improved. However, it is also possible for a solvent suitable for flushing to be fed from an additional tank (not illustrated). As an alternative, or in addition, the accumulation filter 16, 16a, 16b of the measuring cell 12 can be cleaned by ultrasound.

A capacitive signal is preferably used in the measuring cell 7, 12 as a measure of the oil concentration in the water. An oil concentration of the water flowing through is measured in a throughflow measuring cell 7 according to the invention. An accumulated oil concentration is measured in an accumulation filter 16, 16a, 16b in an accumulation measuring cell 12 according to the invention. In both cases, an oil concentration in the water can be enriched in a separating filter 2 connected upstream by a known factor or a factor which can be determined.

The mode of operation of the sensor 1 is based on the fact that the capacitance is lowered with respect to clean water by the oil component in the water. With the accumulation filter 16, 16a, 16b an absolute signal specifies the total embedded oil concentration and a differential signal specifies the instantaneous inflowing oil concentration.

An interval is intended to comprise a longer measuring cycle and a shorter calibration and/or flushing cycle. The measuring cell 7, 12 can also comprise a plurality of accumulation filters 16a, 16b with alternating measuring and flushing cycles, the measuring cycles supplementing or overlapping, one another in time in such a way that an impedance signal of the measuring cell 7, 12 can be measured permanently, and the flushing cycles alternate with one another in such a way that each filter 16a, 16b is flushed over an adequately long time.

In the exemplary embodiment according to FIG. 3, the measuring cell 7, 12 has exactly two accumulation filters 16a, 16b, which are flowed through in series one behind another. In a first work operation (FIG. 3a), the first accumulation filter 16a runs through a measuring cycle and the second accumulation filter 16b runs through a calibration and/or flushing cycle. In a second work operation (FIG. 3b), the first accumulation filter 16a runs through a calibration and/or flushing cycle and the second accumulation filter 16b runs through a measuring cycle. In a further work operation (FIG. 3c) it can be that in order to fix an offset signal only one accumulation filter 16a is flowed through and an offset measurement is carried out at the other accumulation filter 16b. Thereafter, a second work operation (FIG. 3d) is carried out again, but now with a new offset at the filter 16b.

Thus, in this configuration a current measuring signal is permanently generated in the measuring cell 7, 12, and at the same time the non-measuring accumulation filter 16a or 16b is flushed and/or its new offset value is determined as a measure of the total quantity of oil embedded. A high degree of availability and long service life are thereby ensured without manual maintenance.

An oil-in-water sensor 1 for carrying out the above method is also the subject of the invention. In accordance with FIGS. 1 and 2, the sensor 1 comprises means 4, 6a; 10a–10c, 101 for feeding oil-contaminated water to a measuring cell 7, 12 which is connected to measuring means 19, 19a for impedance measurement. According to the invention, the sensor 1 further comprises means 2, 5, 6b, 8; 10b, 10c, 11a, 11b, 102 for self-calibration and/or for self-flushing of the measuring cell 7, 12 and control means 19, 19b for automatically activating the latter. Detailed exemplary embodiments now follow.

In accordance with FIG. 1, the means for self-calibration 2, 5, 6b, 8 may comprise a cross-flow filter 2 with an inlet 3 for oil-contaminated water. The first outlet 4 for oil-enriched water and the second outlet 5 for cleaned water can be connected in an alternating fashion to the measuring cell 7, 12 via controllable valves 6a, 6b. The cross-flow filter 2 advantageously has a second inlet 8 for clean water for the purpose of its own cleaning.

In accordance with FIG. 2, the means for self-flushing 10b, 10c, 11a, 11b, 102 may comprise two flushing lines 102 parallel to the measuring cell 12, it being possible for the measuring cell 12 to be separated from a measuring line 101 by first valves 10b, 10c and to be connected to the flushing lines 102 in the back-flushing direction via second valves 11a, 11b. 9 denotes a feed line from a separator tank, and 10a a pump. The control means 19, 19b advantageously comprise an electronic control system 19 and control signal lines 19b which are configured for automatic control of the valves 10b, 10c; 11a, 11b.

Figure 4A:
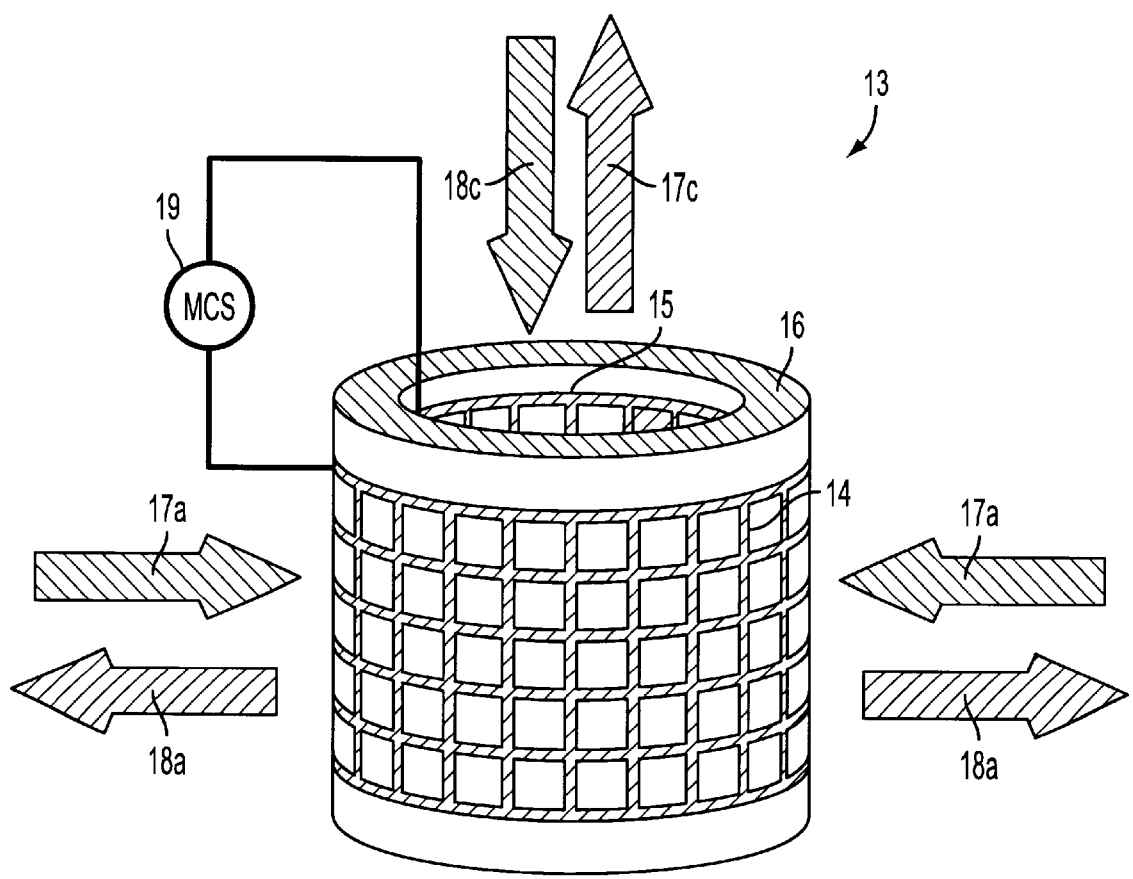

In accordance with FIG. 4, one accumulation filter 16 of the measuring cell 7, 12 is a cylindrical ring-type filter 13 which has an outer electrode 14 and an inner electrode 15 on the cylinder outer surface and a radial connection 17a, 18a and an axial connection 17c, 18c (FIG. 4a). The cylindrical filter 13 according to the invention is distinguished by a large filter surface, pressure resistance, compact design and the ease with which it can be installed.

Figure 4B:
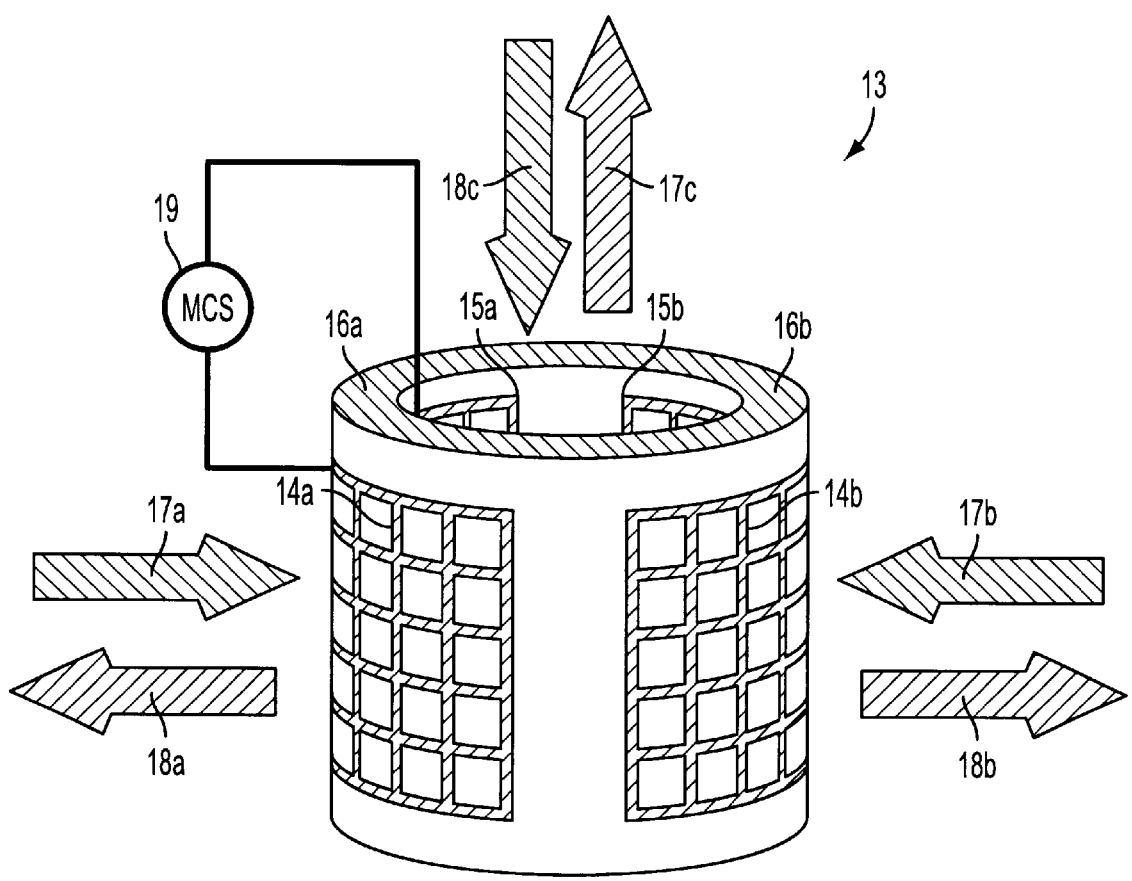

The cylindrical ring-type filter 13 in each case advantageously has two half-shell outer electrodes 14a, 14b and inner electrodes 15a, 15b as well as two separate radial connections 17a, 18a; 17b, 18b (FIG. 4b). Moreover, it is also possible in a simple way for a plurality of radial connections for a plurality of partial filters 16a, 16b with appropriately segmented electrodes 14a, 14b, 15a, 15b to be implemented. Two axial connections going upward and downward can also be made.

The accumulation filter 16, 16a, 16b of the measuring cell 7, 12 is to be a ceramic filter 16, 16a, 16b with a pore size which is water-pervious and oil-absorbing, or a polyethylene fibrid filter. The porous ceramic serves principally for mechanical deposition of oils or, in general, hydrocarbons or (toxic) additives. Hydrocarbons are also embedded in the polyethylene fibrid filter by their chemical affinity to the filter material. The separating filter 2 can be of corresponding design.

The invention specifies an oil-in-water sensor 1 which is capable of everyday use, has a long service life, is suitable for continuous real time measurements of oil contamination in the 10 ppm range, and can be used at inaccessible locations.

List of Reference Numerals

1 Oil-in-water sensor
2 Separating filter, cross-flow filter

3 Inlet
4 First outlet
5 Second outlet
6a, 6b Valves
7, 12 Capacitive measuring cell
8 Second inlet
9 Feed line from separator tank
101 Throughflow line, measuring line
102 Reverse flow line, flushing line
10a Pump
10b, 10c Valves
11a, 11b Valves
13 Capacitive ring-type filter, ceramic filter
14 Outer electrode
15 Inner electrode
16 Ceramic filter, plastic filter
16a, 16b Accumulation filter, oil accumulator
17a, 17b Radial inflow
18a, 18b Radial outflow
17c Axial outflow
18c Axial inflow
19 Measuring apparatus, electronic measurement and control system
19a Measuring signal lines
19b Control signal lines

What is claimed is:

1. A method for oil-in-water measurement, comprising:
   feeding oil-contaminated water to a measuring cell; and
   measuring an electrical impedance signal of the measuring cell, wherein the measuring cell is calibrated and/or flushed automatically at periodic intervals, and wherein an interval comprises a longer measuring cycle and a shorter calibration and/or flushing cycle.

2. The method as claimed in claim 1, comprising:
   permanently measuring an impedance signal of the measuring cell using a plurality of accumulation filters with alternating measuring and flushing cycles which supplement one another.

3. The method as claimed in claim 2, wherein at least one of the following steps is performed:
   a) a capacitance signal is used in the measuring cell as a measure of the oil concentration in the water;
   b) an oil concentration of the water flowing through, or an oil concentration accumulated in an accumulation filter of the measuring cell, is measured in the measuring cell; and
   c) an oil concentration in the water is enriched in a separating filter connected upstream by a known factor.

4. The method as claimed in claim 1, wherein at least one of following steps is performed:
   a) during calibration, the measuring cell is flowed through by clean water and a calibration signal is formed;
   b) during flushing, the measuring cell is flowed through backward by water; and
   c) during flushing, an accumulation filter of the measuring cell is cleaned by ultrasound.

5. The method as claimed in claim 1, wherein at least one of the following steps is performed:
   a) a capacitance signal is used in the measuring cell as a measure of the oil concentration in the water;
   b) an oil concentration of the water flowing through, or an oil concentration accumulated in an accumulation filter of the measuring cell, is measured in the measuring cell; and
   c) an oil concentration in the water is enriched in a separating filter connected upstream by a known factor.

6. The method as claimed in claim 1, wherein, during flushing, the measuring cell is flowed through backward with at least one of oil-contaminated water and a solvent.

7. An oil-in-water sensor for carrying out the method recited in claim 1, the oil-in-water sensor comprising:
   means for feeding oil-contaminated water to a measuring cell which is connected to measuring means for impedance measurement;
   means for at least one of self-calibration and self-flushing of the measuring cell; and
   control means for automatically activating the means for self-calibration and/or for self-flushing.

8. The method as claimed in claim 1, wherein at least one of the following steps is performed:
   a) a capacitance signal is used in the measuring cell as a measure of the oil concentration in the water;
   b) an oil concentration of the water flowing through, or an oil concentration accumulated in an accumulation filter of the measuring cell, is measured in the measuring cell; and
   c) an oil concentration in the water is enriched in a separating filter connected upstream by a known factor.

9. A method for oil-in-water measurement, comprising:
   feeding oil-contaminated water to a measuring cell; and
   measuring an electrical impedance signal of the measuring cell, wherein the measuring cell is calibrated and/or flushed automatically at periodic intervals, and wherein:
   a) the measuring cell has exactly two accumulation filters which are flowed through in series one behind another,
   b) in a first work operation, a first of the two accumulation filters is operated in a measuring cycle and a second of the two accumulation filters is operated in at least one of a calibration cycle and a flushing cycle, and
   c) in a second work operation, the first accumulation filter is operated in at least one of a calibration cycle and a flushing cycle, and the second accumulation filter is operated in a measuring cycle.

10. The method as claimed in claim 9, wherein to fix an offset signal, only one of the two accumulation filters is flowed through, and an offset measurement is carried out at the other of the two accumulation filters.

11. An oil-in-water sensor comprising:
    means for feeding oil-contaminated water to a measuring cell which is connected to measuring means for impedance measurement;
    means for at least one of self-calibration and self-flushing of the measuring cell; and
    control means for automatically activating the means for self-calibration and/or for self-flushing, wherein the means for self-calibration comprise:
    a cross-flow filter having a first outlet for oil-enriched water, and a second outlet for cleaned water, connected in an alternating fashion to the measuring cell via controllable valves.

12. The oil-in-water sensor as claimed in claim 11, comprising at least one of:
    a) an accumulation filter of the measuring cell formed as a ceramic filter with a pore size which is water-pervious and oil-absorbing; and
    b) an accumulation filter of the measuring cell formed as a polyethylene fibrid filter.

13. The oil-in-water sensor as claimed in claim 11, wherein for cleaning purposes the cross-flow filter has a second inlet for clean water.

14. The oil-in-water sensor as claimed in claim 11, comprising at least one of:
   a) an accumulation filter of the measuring cell formed as a ceramic filter with a pore size which is water-pervious and oil-absorbing; and
   b) an accumulation filter of the measuring cell formed as a polyethylene fibrid filter.

15. An oil-in-water sensor, comprising:
   means for feeding oil-contaminated water to a measuring cell which is connected to measuring means for impedance measurement; and
   means for self-flushing of the measuring cell, which means for self-flushing comprise two flushing lines parallel to the measuring cell, and wherein the measuring cell can be separated from a measuring line by first valves, and can be connected to the flushing lines in a back-flushing direction via second valves.

16. The oil-in-water sensor as claimed in claim 15, comprising:
   control means for automatically activating the means for self-flushing.

17. The oil-in-water sensor as claimed in claim 15, comprising:
   an electronic control system and control signal lines which are configured for automatic control of the valves.

18. The oil-in-water sensor as claimed in claim 15, wherein the measuring cell includes an accumulation filter configured as a cylindrical ring-type filter which has an outer electrode on an outer cylinder surface and an inner electrode on an inner cylinder surface and a radial connection and an axial connection.

19. The oil-in-water sensor as claimed in claim 15, comprising at least one of:
   a) an accumulation filter of the measuring cell formed as a ceramic filter with a pore size which is water-pervious and oil-absorbing; and
   b) an accumulation filter of the measuring cell formed as a polyethylene fibrid filter.

20. An oil-in-water sensor, comprising:
   means for feeding oil-contaminated water to a measuring cell, which is connected to measuring means for impedance measurement; and
   means for self-flushing and/or self-calibration of the measuring cell, wherein the measuring cell comprises a cylindrical ring-type accumulation filter, which accumulation filter has an outer electrode on an outer cylinder surface and an inner electrode on an inner cylinder surface and a radial connection and an axial connection.

21. The oil-in-water sensor as claimed in claim 20, wherein the cylindrical ring-type filter includes two half-shell outer electrodes and inner electrodes, as well as two separate radial connections.

22. The oil-in-water sensor as claimed in claim 20, wherein the means for self-calibration comprise:
   a cross-flow filter having a first outlet for oil-enriched water, and a second outlet for cleaned water, connected in an alternating fashion to the measuring cell via controllable valves.

23. The oil-in-water sensor as claimed in claim 20, comprising:
   control means for automatically activating the means for self-flushing and/or self-calibration.

24. A method for oil-in-water measurement, comprising:
   feeding oil-contaminated water to a measuring cell;
   measuring an electrical impedance signal of the measuring cell;
   enriching an oil concentration in the water by a known factor in a separating filter connected upstream from the measuring cell, the separating filter comprising a first outlet for oil-enriched water and a second outlet for cleaned water; and
   calibrating the measuring cell automatically at periodic intervals with water output from the second output of the separating filter.

25. A method for oil-in-water measurement, comprising:
   feeding oil-contaminated water to a measuring cell, the measuring cell comprising a cylindrical ring-type accumulation filter, which accumulation filter has an outer electrode on an outer cylinder surface and an inner electrode on an inner cylinder surface and a radial connection and an axial connection; and
   measuring an oil concentration accumulated in the accumulation filter through an electrical impedance signal of the measuring cell, the measuring cell being flushed and/or calibrated automatically at periodic intervals.

26. A method for oil-in-water measurement, comprising:
   feeding oil-contaminated water to a measuring cell, an accumulation filter being arranged in the measuring cell, and
   measuring oil concentration accumulated in the accumulation filter through an electrical impedance signal of the measuring cell, the measuring cell being flushed automatically at periodic intervals, and during flushing, the measuring cell being flowed through backward by water, wherein an oil concentration in the water is enriched in a separating filter connected upstream by a known factor.

* * * * *